(12) United States Patent
VanMechelen et al.

(10) Patent No.: US 6,670,137 B2
(45) Date of Patent: Dec. 30, 2003

(54) DIFFERENTIAL DIAGNOSIS OF NEUROLOGICAL DISEASES

(75) Inventors: Eugeen VanMechelen, Nazareth-Eke (BE); Hugo Vanderstichele, Gent (BE); Frank Hulstaert, Gentbrugge (BE)

(73) Assignee: Innogenetics N.V. (BE)

( * ) Notice: Subject to any disclaimer, the term of this patent is extended or adjusted under 35 U.S.C. 154(b) by 137 days.

(21) Appl. No.: 09/892,835

(22) Filed: Jun. 27, 2001

(65) Prior Publication Data

US 2002/0019016 A1 Feb. 14, 2002

Related U.S. Application Data

(60) Provisional application No. 60/218,907, filed on Jul. 18, 2000.

(30) Foreign Application Priority Data

Jun. 30, 2000 (EP) .............................................. 00870151

(51) Int. Cl.[7] ...................... G01N 33/53; G01N 33/567; G01N 33/566; C07K 1/00
(52) U.S. Cl. ........................ 435/7.1; 435/7.21; 435/7.8; 436/501; 530/350; 530/300; 530/387.1
(58) Field of Search ................................. 435/7.1, 7.21; 530/350, 300, 387.1

(56) References Cited

U.S. PATENT DOCUMENTS

| | | | |
|---|---|---|---|
| 5,601,985 A | 2/1997 | Trojanowski et al. | ........ 435/7.1 |
| 6,008,024 A | 12/1999 | Vandermeeren et al. | . 435/70.21 |

FOREIGN PATENT DOCUMENTS

| | | | |
|---|---|---|---|
| WO | WO95/17429 | 6/1995 | ........... C07K/16/18 |

OTHER PUBLICATIONS

Hulstaert et al., 1999, Neurology, 52, pp. 1555–1562.*
Ishiguro et al., 1999, Neuroscience Letters, 270, pp. 91–94.*
Strong et al., 1995, Alzheimer Disease and Associated Disorders, vol. 9, No. 4, pp. 218–222.*
Vanmechelen et al,—Chemical Abstract, XP–002154344, Abstract No. 117039a, (Aug. 28, 2000), vol. 133, No. 9.
Strong C et al, Database Medline, *US National Library of Medicine (NLM)*, Bethesda, MD, XP002154345, Database Accession No. 96307681 (1995).
Arai, Hiroyuki et al., "Cerebrospinal fluid tau levels in neurodegerative diseases with distinct tau–related pathology," *Bichemical and Biophisical Research Communications*, 236:262–264 (1997).
Colosimo, Carl et al., "Some specific clinical features differentiate multiple system atrophy (striatonigral variety) from Parkinson's disease," *Arch. Neurol.* 52:294–298 (1995).

Sjögren, M., et al., "Both total and phosphorylated tau are increased in Alzheimer's isease," *J. Neurol. Neurosurg. Psychiatry*, 70:624–630 (2001).
Green, A.J.E et al., "Increased tau in the cerebrospinal fluid of patients with frontotemporal dementia and Alzheimer's disease," *Neuroscience Letters* 259:133–135 (1999).
Knopman D.S. et al. "Practice parameter: diagnosis of dementia (an evidence–based review) Report of the quality standards subcommittee of the American Academy of Neurology," *Neurology* 56:1143–1153 (2001).
Lantos, P.L. "Unusual Dementias" in *Alzheimer's disease and related disorders*, ed. By Khalid Iqbal, John Wiley & Sons, New York, (1999) pp. 509–522.
Lopez, O.L. et al. "Accuracy of four clinical diagnostic criteria for the diagnosis of neurodegenerative dementias" *Neurology*, 53:1292–1299 (1999).
McKeith, I.G. et al. "Report of the second dementia with Lewy body international workshop: diagnosis and treatment," *Neurology*, 53:902–905 (1999).
McKeith, I.G. et al. "Diagnosing dementia with Lewy bodies" *The Lancet*, 354:1227–1228 (1999).
Molina, J.A. et al. "Tau protein concentrations in cerebrospinal fluid of non–demented Parkinson's disease patients," *Neuroscience Letters*, 238:139–141 (1997).
Vermersch, P. et al., *C.R. Acad. Sci. Paris, Sciences de la vie*. 318:439–445 (1995) (English Abstract).
Rinne, J.O. et al. "Corticobasal degeneration: A Clinical study of 36 cases,"*Brain*, 117:1183–1196 (1994).
Stoessl, A.J. and Jean Rivest "Differential diagnosis of Parkinsonism," *Canadian J. Neurol. Sci.*, 26:Suppl. 2–S1–S4 (1999).
Urakami, K. et al. "A comparison of tau protein in cerebrospinal fluid between corticobasal degeneration and progressive supranuclear palsy" *Neuroscience Letters*, 259:127–129 (1999).

\* cited by examiner

*Primary Examiner*—John Ulm
*Assistant Examiner*—Olga N. Chernyshev
(74) *Attorney, Agent, or Firm*—Howrey Simon Arnold & White, LLP

(57) ABSTRACT

The present invention provides a method for the differential diagnosis of an individual suffering from Alzheimer's disease versus and individual suffering from another neurological disease. More specifically, the present invention provides a method for the differential diagnosis of an individual suffering from Alzheimer's disease versus an individual suffering from dementia with Lewy bodies, versus an individual suffering from Parkinson's disease without dementia, versus an individual suffering from multi-system atrophy and/or versus an individual suffering from progressive supranuclear palsy, said method characterized that phospho-tau is used as a neurological marker.

5 Claims, No Drawings

DIFFERENTIAL DIAGNOSIS OF NEUROLOGICAL DISEASES

This application is a non-provisional application claiming priority to EP 00870151.8 filed Jun. 30, 2000 and U.S. S No. 60/218,907 filed Jul. 18, 2000.

FIELD OF THE INVENTION

The present invention relates to the field of the diagnosis of neurological diseases. The present invention provides a new method for the differential diagnosis of Alzheimer's disease versus other neurological diseases. More particular, the present invention provides a method for the differential diagnosis of Alzheimer's disease versus dementia with Lewy bodies, versus Parkinson's disease without dementia, versus multi-system atrophy and/or versus progressive supranuclear palsy.

BACKGROUND OF THE INVENTION

The use of tau and phospho-tau as neurological markers in the diagnosis of neurological diseases has been postulated (Blennow et al., 1995; Vigo-Pelfrey et al., 1995; Andreasen et al., 1998; Andreasen et al., 1999a; Ishiguro et al., 1999). The microtubule-associated protein tau is a major protein component of paired helical filaments (PHF) and neurofibrillar tangles (NFT), associated with Alzheimer's disease (Brion et al., 1985; Delacourte and Defossez, 1986; Grundke-Iqbal et al., 1986; Kosik et al., 1986; Wood et al., 1986; Kondo et al., 1988). Tau protein exists in different isoforms, of which 4 to 6 are found in adult brain but only 1 isoform is detected in fetal brain. The diversity of the isoforms is generated from a single gene on human chromosome 17 by alternative mRNA splicing (Himmler, 1989; Goedert et al., 1989; Andreadis et al., 1992). The most striking feature of tau protein, as deduced from molecular cloning, is a stretch of 31 or 32 amino acids, occurring in the carboxy-terminal part of the molecule, which can be repeated either 3 or 4 times. Additional diversity is generated through 29 or 58 amino acid-long insertions in the $NH_2$-terminal part of tau molecules (Goedert et al., 1989). In vivo tau promotes microtubule assembly and stability in the axonal compartment of neurons by interactions involving its microtubule binding domain which is localized in the repeat region of tau (255–381) (Lewis et al., 1988). In normal circumstances adult brain contains 2–3 mole phosphate per mole of tau (Selden and Pollard, 1983; Ksiezak-Reding et al., 1992). Phosphorylation of different sites in normal tau as studied in rat and humans is dependent on the developmental state (Lee et al., 1991; Bramblett et al., 1993; Goedert et al., 1993). Tau variants of 60, 64 and 68 kDa arising as a consequence of phosphorylation have been detected in brain areas showing neurofibrillary tangles (Delacourte et al., 1990; Goedert et al., 1992; Flament et al., 1990, Greenberg and Davies, 1990). These brains contain 6–8 mole phosphate per mole tau (Ksiezak-Reding et al., 1992). In tau isolated from PHF (PHF-tau), phosphorylation occurs at several positions (Iqbal et al., 1989; Lee et al., 1991; Hasegawa et al., 1992; Hanger et al., 1998; Buee et al., 1999).

Alzheimer's disease (AD) and frontotemporal dementia (FTD) are the most common types of primary degenerative dementia associated with a tau pathology, having a prevalence of respectively 42–75% and 8–10% (Brun, 1993; Gustafson, 1993; Ebly et al., 1994). Filamentous tau pathology i.e. neurofibrillary tangles (NFT), are consistently found in AD (Tomlinson and Corsellis, 1984) but may also be found in FTD (Spillantini and Goedert, 1998). Pathological tau proteins are found both in AD and FTD (Vermersch et al., 1995; Delacourte et al., 1996). Studies on brain tissue, however, have suggested that the tau pathology differs between AD and FTD, possibly being related to the degree of phosphorylation (Delacourte et al., 1996). Other forms of dementia associated with a tau pathology include familial FTD, progressive supranuclear palsy (PSP), corticobasal degeneration (CBD) and subacute sclerosing panencephalitis. The role of hyperphosphorylation in the pathology of these tauopathies is at present not well understood.

Dementia with Lewy bodies (DLB) is an illness that presents with progressive dementia or psychosis. Parkinsonian signs, which may be absent or mild at the onset, eventually become common and rigidity is usually severe. Lewy bodies are found profusely in the brainstem, basal forebrain, hypothalamic nuclei and neocortex. Dementia with Lewy bodies is characterized by the relative absence of tangles and hyperphosphorylated tau in the brain. Parkinson's disease (PD) is a type of Lewy Body disease occurring in the middle or late life, with very gradual progression and a prolonged course. It can be considered as an example of neuronal system disease, involving mainly the nigrostriatal dopaminergic system. Dementia with Lewy bodies was recently defined as a special form of dementia requiring differential patient management (Lebert et al., 1998; McKeith et al., 1999). Dementia with Lewy bodies, which is sensitive to neuroleptics, is clinically very difficult to differentiate from Alzheimer's disease (McKeith et al., 1996; Ballard et al., 1998). Most patients (more than 75%) are neuropathologically defined as Alzheimer's disease patients while it is estimated that 15 to 25% of the clinically diagnosed Alzheimer's disease patients have dementia with Lewy bodies (Hooten et al., 1998). As dementia with Lewy bodies is more susceptible to acetylcholinesterase treatment, differentiation of dementia with Lewy bodies from Alzheimer's disease is essential for optimization of treatment (Levy et al., 1994; Perry et al., 1994; Wilcock et al., 1994).

Cerebrospinal fluid (CSF)-β-amyloid and CSF-tau have been validated to discriminate Alzheimer's disease from normal aging, depression and Parkinson's disease (Galasko et al., 1998; Kanai et al., 1998; Hulstaert et al., 1999) and these markers are well suited for the differential diagnosis of these disorders (Andreasen et al., 1999b). More controversial, however, is their role in the discrimination of Alzheimer's disease from closely related conditions such as dementia with Lewy bodies and from other dementia associated with tau pathology such as frontotemporal dementia, multi-system atrophy (MSA) and/or progressive supranuclear palsy. At present, no accurate methods exist for the differential diagnosis of these neurological diseases.

AIMS OF THE INVENTION

It is an aim of the present invention to provide a method for the differential diagnosis of an individual suffering from Alzheimer's disease versus an individual suffering from another neurological disease.

It is an aim of the present invention to provide a method for the differential diagnosis of an individual suffering from Alzheimer's disease versus an individual suffering from dementia with Lewy bodies.

It is an aim of the present invention to provide a method for the differential diagnosis of an individual suffering from Alzheimer's disease versus an individual suffering from Parkinson's disease without dementia.

It is an aim of the present invention to provide a method for the differential diagnosis of an individual suffering from Alzheimer's disease versus an individual suffering from multi-system atrophy.

It is an aim of the present invention to provide a method for the differential diagnosis of an individual suffering from Alzheimer's disease versus an individual suffering from progressive supranuclear palsy.

It is an aim of the present invention to provide an in vitro method for the differential diagnosis of an individual suffering from Alzheimer's disease versus an individual suffering from another neurological disease.

It is an aim of the present invention to provide an in vitro method for the differential diagnosis of an individual suffering from Alzheimer's disease versus an individual suffering from dementia with Lewy bodies.

It is an aim of the present invention to provide an in vitro method for the differential diagnosis of an individual suffering from Alzheimer's disease versus an individual suffering from Parkinson's disease without dementia.

It is an aim of the present invention to provide an in vitro method for the differential diagnosis of an individual suffering from Alzheimer's disease versus an individual suffering from multi-system atrophy.

It is an aim of the present invention to provide an in vitro method for the differential diagnosis of an individual suffering from Alzheimer's disease versus an individual suffering from progressive supranuclear palsy.

It is an aim of the present invention to provide a diagnostic kit for the differential diagnosis of an individual suffering from Alzheimer's disease versus an individual suffering from another neurological disease.

It is an aim of the present invention to provide a diagnostic kit for the differential diagnosis of an individual suffering from Alzheimer's disease versus an individual suffering from dementia with Lewy bodies.

It is an aim of the present invention to provide a diagnostic kit for the differential diagnosis of an individual suffering from Alzheimer's disease versus an individual suffering from Parkinson's disease without dementia.

It is an aim of the present invention to provide a diagnostic kit for the differential diagnosis of an individual suffering from Alzheimer's disease versus an individual suffering from multi-system atrophy.

It is an aim of the present invention to provide a diagnostic kit for the differential diagnosis of an individual suffering from Alzheimer's disease versus an individual suffering from progressive supranuclear palsy.

It is an aim of the present invention to provide a method to screen or monitor the effect of compounds which prevent dementia with Lewy bodies, Parkinson's disease without dementia, multi-system atrophy and/or progressive supranuclear palsy or which treat an individual suffering from dementia with Lewy bodies, an individual suffering from Parkinson's disease without dementia, an individual suffering from multi-system atrophy and/or an individual suffering from progressive supranuclear palsy.

TABLE 1

Demographic data and CSF results by different diagnostic groups.

| Group | Subjects, n (M/F) | Age, y, median, (range) | MMSE n | MMSE Median (p25–p75) | Aβ42, pM, median (p25–p75) | Tau, pM, median (p25–p75) | Ptau(181), pM, median (p25–p75) |
|---|---|---|---|---|---|---|---|
| AD | 80 (35/45) | 72 (53–86) | 78 | 22 (14–24) | 69.2 (47.1–96.0)* | 13.2 (9.4–17.0)* | 14.7 (11.6–19.1)* |
| Controls | 40 (20/20) | 70 (56–84) | 20 | 30 (29–30) | 99.3 (75.5–145.3)$ | 3.0 (2.1–4.0)$ | 7.8 (6.4–8.9)$ |
| FTD | 69 (42/27) | 67 (40–94) | 61 | 22 (16–25) | 90.3 (67.0–132.5)$ | 7.5 (5.2–10.8)£,$ | 9.4 (8.2–12.3)£,$ |
| LBD | 43 (35/8) | 72 (61–87) | 37 | 19 (14–24) | 72.2 (53–103)£ | 5.7 (1.6–9.0)$ | 8.1 (6.1–10.0)$ |
| PD | 15 (8/7) | 70 (51–79) | 1 | 23 | 72.3 (58.1–99.1) | 4.2 (2.2–7.6)$ | 7.4 (6.9–8.8)$ |
| MSA | 16 (11/5) | 64 (42–77) | 3 | 20 (20–22) | 91.5 (41.9–113.4) | 5.3 (3.8–8.3)$ | 7.6 (6.2–10.9)$ |
| PSP | 15 (11/4) | 67 (64–76) | 4 | 26 (21–27) | 96.6 (82.2–101.1) | 2.8 (2.0–4.5)$ | 6.9 (6.1–7.5)$ |
| CBD | 5 (0/5) | 70 (57–75) | 4 | 13 (12–15) | 70.2 (43.2–71.2) | 12.9 (9.8–15.4) | 12.7 (9.1–13.1) |

AD = Alzheimer's disease,
FTD = frontotemporal dementia,
DLB = dementia with Lewy bodies,
PD = Parkinson's disease,
MSA = multi-system atrophy,
PSP = progressive supranuclear palsy,
CBD = corticobasal degeneration
*Significantly different from controls (p < 0.001)
£Significantly different from controls (p < 0.05)
$Significantly different from AD (p < 0.001)

TABLE 2

Comparison of the discriminative power of CSF-tau and CSF-phopsho-tau using ROC analysis.

| Groups | CSF-tau (AUC ± SE) | CSF-phospho-tau (AUC ± SE) | p-value |
|---|---|---|---|
| AD vs controls (n = 40) | 0.862 ± 0.038 | 0.897 ± 0.032 | 0.191 |
| AD vs FTD (n = 69) | 0.711 ± 0.045 | 0.754 ± 0.044 | 0.049 |
| AD vs DLB (n = 43) | 0.782 ± 0.048 | 0.839 ± 0.042 | 0.039 |
| AD vs Parkinson related conditions (n = 46) | 0.873 ± 0.035 | 0.864 ± 0.037 | 0.319 |

Receiver operating curve (ROC) analysis with area under the curve (AUC) and standard error (SE) calculated according to Hanley and McNeil.
AD = Alzheimer's disease,
FTD = frontotemporal dementia,
DLB = dementia with Lewy bodies, Parkinson-related conditions include Parkinson's disease without dementia (n = 15), multiple system atrophy (n = 16) and progressive supranuclear palsy (n = 15).

DETAILED DESCRIPTION OF THE INVENTION

The present invention relates to a method for the differential diagnosis of an individual suffering from Alzheimer's disease (AD) versus an individual suffering from another neurological disease characterized that phospho-tau is used as a neurological marker. More specifically, the present invention relates to a method as described above comprising the steps of:

determining the level of phospho-tau in said individual;

inference that said individual is suffering from a neurological disease other than Alzheimer's disease by comparing the obtained level of phospho-tau in said individual with the level of phospho-tau in individuals suffering from Alzheimer's disease, whereby a decreased level of phospho-tau being an indication that said individual is suffering from a neurological disease other than Alzheimer's disease.

'Differential diagnosis of an individual suffering from a neurological disease versus an individual suffering from another neurological disease' as used in the present invention refers to the discrimination between said first neurological disease and other neurological diseases in this way that a certain neurological disease or a certain cause of neurological disorder in an individual is associated with a certain neurodegenerative condition of said individual. The method of the present invention allows the differential diagnosis of an individual suffering from Alzheimer's disease versus an individual suffering from a neurological disease other than Alzheimer's disease. In a specific embodiment, the present invention allows the differential diagnosis of an individual suffering from Alzheimer's disease (AD) versus an individual suffering from dementia with Lewy bodies (DLB). In another specific embodiment, the present invention allows the differential diagnosis of an individual suffering from Alzheimer's disease (AD) versus an individual suffering from Parkinson's disease (PD) without dementia. In another specific embodiment, the present invention allows the differential diagnosis of an individual suffering from Alzheimer's disease (AD) versus an individual suffering from multi-system atrophy (MSA). In another specific embodiment, the present invention allows the differential diagnosis of an individual suffering from Alzheimer's disease (AD) versus an individual suffering from progressive supranuclear palsy (PSP). Alzheimer's disease, dementia with Lewy bodies, Parkinson's disease without dementia, multi-system atrophy and progressive supranuclear palsy as well as other neurological diseases have been described in detail by Wilson et al. (1991) and McKeith et al. (1999).

The present invention is based on the finding that the level of phospho-tau in CSF from individuals suffering from dementia with Lewy bodies, from PD without dementia, from MSA or from PSP is significantly decreased compared to the level of phospho-tau in CSF from individuals suffering from Alzheimer's disease. The indication that the level of phospho-tau differs between said neurological diseases, forms the basis for the development of a diagnostic test for the differential diagnosis of said neurological diseases in an individual. Accordingly, the present invention relates to a method for the differential diagnosis of an individual suffering from Alzheimer's disease versus an individual suffering from dementia with Lewy bodies, versus an individual suffering from Parkinson's disease without dementia, versus an individual suffering from multi-system atrophy and/or versus an individual suffering from progressive supranuclear palsy, said method characterized that phopho-tau is used as a neurological marker.

The method of the invention thus comprises the step of determining the level of phospho-tau in said individual suspected of suffering from AD, from DLB, from PD without dementia, from MSA or from PSP and comparing it with a previously defined phospho-tau level range characteristic for AD, DLB, PD without dementia, MSA or PSP. A level of phospho-tau falling within the previously defined phospho-tau level range for Alzheimer's disease is an indication that said individual is suffering from AD. A level of phospho-tau falling within the previously defined phospho-tau level range for DLB is an indication that said individual is suffering from DLB. A level of phospho-tau falling within the previously defined phospho-tau level range for PD without dementia is an indication that said individual is suffering from PD without dementia. A level of phospho-tau falling within the previously defined phospho-tau level range for MSA is an indication that said individual is suffering from MSA. A level of phospho-tau falling within the previously defined phospho-tau level range for PSP is an indication that said individual is suffering from PSP.

Accordingly, the present invention relates to a method for the differential diagnosis of an individual suffering from Alzheimer's disease versus an individual suffering from dementia with Lewy bodies, versus an individual suffering from Parkinson's disease without dementia, versus an individual suffering from multi-system atrophy and/or versus an individual suffering from progressive supranuclear palsy, comprising the steps of:

determining the level of phospho-tau in said individual;

inference that said individual is suffering from DLB, from PD without dementia, from MSA and/or from PSP by comparing the obtained level of phospho-tau in said individual with the level of phospho-tau in individuals suffering from AD, whereby a decreased level of phospho-tau being an indication that said individual is suffering from DLB, from PD without dementia, from MSA and/or from PSP.

The level of phospho-tau can be detected in vitro as well as in vivo. The method for the in vitro detection of the level of phospho-tau in an individual comprises the steps of obtaining a sample from said individual, determining the level of phospho-tau in said sample and comparing it with a previously defined phospho-tau level range for said neurological disease.

The term 'sample' refers to any source of biological material, for instance body fluids, brain extract, peripheral blood or any other sample comprising phospho-tau protein. In a preferred embodiment, the level of phospho-tau is determined in vitro by analysis of the level of phospho-tau in a body fluid sample of the patient. The term 'body fluid' refers to all fluids that are present in the human body including but not limited to blood, lymph, urine and cerebrospinal fluid (CSF) comprising phospo-tau protein. The blood sample may include a plasma sample or a serum sample.

In a preferred embodiment of the present invention the level of phospho-tau is determined in a cerebrospinal fluid sample taken from the patient. In accordance, the present invention relates to a method as described above, comprising the steps of:

obtaining a cerebrospinal fluid sample from said individual;

determining the level of phospho-tau in said cerebrospinal fluid sample;

inference that said individual is suffering from a neurological disease other than AD such as DLB, PD without dementia, MSA and/or PSP by comparing the obtained level of phospho-tau in said cerebrospinal fluid sample with the level of phospho-tau in a cerebrospinal fluid sample from individuals suffering from AD, whereby a decreased level of phospho-tau being an indication that said individual is suffering from another neurological disease such as DLB, PD without dementia, MSA and/or PSP.

The level of phospho-tau as measured in the CSF of the individual suspected to suffer from DLB, from PD without dementia, from MSA and/or from PSP is compared with the level of phospho-tau in the CSF of an individual suffering from AD. A decreased level of CSF-phospho-tau is interpreted as an indication of the individual suffering from DLB, from PD without dementia, from MSA and/or from PSP.

Phospho-tau include all forms of tau that have a phosphorylation on any position of the tau protein sequence, but more specifically it refers to phosphorylations on amino acid positions that are not phosphorylated in human normal tau isolated from adult individuals not suffering from any neurological disorder.

'A decreased level of phospho-tau' means that the level of phospho-tau measured in the patient is lower than the level of phospho-tau measured in patients suffering form AD. Phospho-tau can be quantified by any method known in the art, including but not limited to the use of antibodies. In a preferred embodiment, phospho-tau is quantified by an immunoassay comprising at least the following steps:

obtaining a sample from the patient;

bringing said sample into contact with a monoclonal antibody specifically recognizing phospho-tau, under conditions being suitable for producing an antigen-antibody complex;

detecting the immunological binding of said antibody to said sample.

In another embodiment, phospho-tau can be quantified by a sandwich ELISA comprising the following steps:

obtaining a sample from the patient;

bringing said sample into contact with an antibody (primary antibody or capturing antibody) recognizing phospho-tau, under conditions being suitable for producing an antigen-antibody complex;

bringing said sample into contact with a monoclonal antibody (secondary antibody or detector antibody) specifically recognizing phospho-tau, under conditions being suitable for producing an antigen-antibody complex;

bringing the antigen-antibody complex into contact with a marker either for specific tagging or coupling with said secondary antibody, with said marker being any possible marker known to the person skilled in the art;

possibly also, for standardization purposes, bringing the antibodies in contact with a purified phospho-tau protein or phospho-peptide reactive with both antibodies.

Advantageously, the secondary antibody itself carries a marker or a group for direct or indirect coupling with a marker.

The expression 'recognizing', 'reacting with', 'immunological binding' or 'producing an antigen-antibody complex' as used in the present invention is to be interpreted that binding between the antigen and antibody occurs under all conditions that respect the immunological properties of the antibody and the antigen.

The expression 'specifically recognizing' as used in the present invention is to be interpreted that said antibody is capable of forming an immunological complex with phospho-tau but not with human normal tau.

Any monoclonal antibody that specifically recognizes phospho-tau can be used in said method for the quantification of phospho-tau. Monoclonal antibodies for use in the quantification of phospho-tau include AT8 (WO 93/08302), AT180 and AT270 (WO 95/17429) and AT100 (WO 96/04309). Other antibodies known in the art that specifically recognize phospho-tau can be used as well.

Also fragments derived from these monoclonal antibodies such as Fab, F(ab)'$_2$, ssFv ('single chain variable fragment') and other antibody-like constructs that retain the variable region of the antibody, providing they have retained the original binding properties, can be used in a method of the present invention. Such fragments are commonly generated by, for instance, enzymatic digestion of the antibodies with papain, pepsin, or other proteases. It is well known to the person skilled in the art that monoclonal antibodies, or fragments thereof, can be modified for various uses. Also mini-antibodies and multivalent antibodies such as diabodies, triabodies, tetravalent antibodies and peptabodies can be used in a method of the invention. The preparation and use of these fragments and multivalent antibodies has been described extensively in International Patent Application WO 98/29442.

The monoclonal antibodies used in a method of the invention may be humanized versions of the mouse monoclonal antibodies made by means of recombinant DNA technology, departing from the mouse and/or human genomic DNA sequences coding for H and L chains or from cDNA clones coding for H and L chains. Alternatively the monoclonal antibodies used in a method of the invention may be human monoclonal antibodies. The term 'humanized antibody' means that at least a portion of the framework regions of an immunoglobulin is derived from human immunoglobulin sequences.

The antibodies used in a method of the present invention may be labeled by an appropriate label of the enzymatic, fluorescent, or radioactive type.

The method for the in vivo detection of the level of phospho-tau in an individual comprises the steps of determining the level of phospho-tau in said individual and comparing it with a previously defined phospho-tau level range characteristic for AD, DLB, PD without dementia, MSA or PSP. In an embodiment of the invention, phospho-tau can be quantified by in vivo imaging. Phospho-tau can be quantified in situ by non-invasive methods including but not limited to brain imaging methods described by Arbit et al. (1995), Tamada et al. (1995), Wakabayashi et al. (1995), Huang et al. (1996), Sandrock et al. (1996), Mariani et al. (1997). These in vivo imaging methods may allow the localization and quantification of phospho-tau, for example, by use of labeled antibodies specifically recognizing phospho-tau.

The present invention thus relates to the use of phospho-tau as a neurological marker for the differential diagnosis of an individual suffering from AD versus an individual suffering another neurological disease. The present invention specifically relates to the use of phospho-tau as a neurological marker for the differential diagnosis of an individual suffering from AD versus an individual suffering from DLB, versus an individual suffering from PD without dementia, versus an individual suffering from MSA and/or versus an individual suffering from PSP.

The present invention also relates to the use of phospho-tau as a neurological marker for the manufacture of a diagnostic kit for the differential diagnosis of an individual suffering from Alzheimer's disease versus an individual suffering from another neurological disease. The present invention specifically relates to the use of phospho-tau as a neurological marker for the manufacture of a diagnostic kit for the differential diagnosis of an individual suffering from Alzheimer's disease versus an individual suffering from DLB, versus an individual suffering from PD without dementia, versus an individual suffering from MSA and/or versus an individual suffering from PSP.

The present invention also relates to the use of an antibody that specifically recognizes phospho-tau for the manufacture of a diagnostic kit for the differential diagnosis of an individual suffering from Alzheimer's disease versus an individual suffering from another neurological disease. The present invention specifically relates to the use of an antibody that specifically recognizes phospho-tau for the manufacture of a diagnostic kit for the differential diagnosis of an individual suffering from Alzheimer's disease versus an individual suffering from DLB, versus an individual suffering from PD without dementia, versus an individual suffering from MSA and/or versus an individual suffering from PSP.

In accordance, the present invention also relates to a diagnostic kit for use in the differential diagnosis of an individual suffering from Alzheimer's disease versus an individual suffering from another neurological disease, comprising an antibody that specifically recognizes phopho-tau. The present invention specifically relates to a diagnostic kit for use in the differential diagnosis of an individual suffering from Alzheimer's disease versus an individual suffering from DLB, versus an individual suffering from PD without dementia, versus an individual suffering from MSA and/or versus an individual suffering from PSP, comprising an antibody that specifically recognizes phopho-tau.

A possible kit for carrying out the method of the invention is based on an immunoassay and comprises:

- an antibody (primary antibody) which forms an immunological complex with an epitope of phospho-tau;
- a monoclonal antibody (secondary antibody) which specifically recognizes phospho-tau;
- a marker either for specific tagging or coupling with said secondary antibody;
- appropriate buffer solutions for carrying out the immunological reaction between the primary antibody and the test sample, between the secondary antibody and the test sample and/or between the bound secondary antibody and the marker;
- possibly, a purified phospho-tau protein or a phospho-peptide for standarization purposes.

The present invention further relates to the use of a diagnostic kit as described above for the differential diagnosis of an individual suffering from Alzheimer's disease versus an individual suffering from another neurological disease. The present invention specifically relates to the use of a diagnostic kit as described above for the differential diagnosis of an individual suffering from Alzheimer's disease versus an individual suffering from DLB, versus an individual suffering from PD without dementia, versus an individual suffering from MSA and/or versus an individual suffering from PSP.

The invention also relates to a method to screen or monitor the effect on an individual of compounds which prevent or treat Alzheimer's disease, dementia with Lewy bodies, Parkinson's disease without dementia, multi-system atrophy and/or progressive supranuclear paly.

Throughout this specification and the claims which follow, unless the context requires otherwise, the word "comprise", and variations such as "comprises" and "comprising", will be understood to imply the inclusion of a stated integer or step or group of stated integers or steps but not to the exclusion of any other integer or step or group of integers or steps.

The present invention will now be illustrated by reference to the following examples that set forth particularly advantageous embodiments. However, it should be noted that these examples are illustrative and can not be construed as to restrict the invention in any way.

EXAMPLES

Subjects and Methods 14 university centers involved in CSF research were contacted to participate in a multicenter study. Each center was requested to include 500 µl CSF of exactly 10 AD patients (McKhann et al., 1984) and a minimum of 6 samples from patients with DLB (McKeith et al., 1996) or FTD (Anonymous, 1994). Eight centers complied with these conditions. If CSF was available from patients with PSP (Golbe et al, 1993), CBD (Rinne et al., 1994) and multiple system atrophy (MSA) (Colosimo et al., 1995) they were also included in the study. Age-matched controls without neurological and cognitive problems and Parkinson's disease (PD) without dementia (Langston et al., 1992) were included if 10 samples were available per center.

The study was performed on CSF samples available for research purposes and if required the protocol was reviewed and approved by the local Independent Ethics Committee/Institutional Review Board (IEC/IRB) prior to the study start.

Samples were collected in polypropylene tubes using lumbar puncture. Because it has been demonstrated that freeze-thawing seriously affects $\beta$-amyloid$_{42}$ (A$\beta$42) levels (Andreasen et al., 1999b; Vanderstichele et al., 1998) the number of freeze-thaw cycles was documented. CSF samples that contained>500 red blood cells per microliter were not included.

"All determinations were performed at Innogenetics (Gent, Belgium) using standard kits for CSF-AB42 (K-1080, Innogenetics) (Andreasen et al., 1999b; Vanderstichele et al., 1998), hTau (K-1032, Innogenetics) (Vandermeeren et al., 1993; Blennow et al., 1995; Van de Voorde et al., 1995) and a research version of the INNOTEST PHOSPHO-TAU. The phospho-tau kit is developed using a human-specific antibody, HT7, for capturing and a phospho-threonine-181-specific antibody, AT270, for detection (Goedert et al., 1994). As a standard, a synthetic peptide (Ac-P$_{154}$RGAAPPGQKGQANATRIPAKTPPAPKT(p)PPSSGE$_{187}$-NH$_2$) (SEQ ID NO: 1) with the corresponding threonine 181 phosphorylated was used. The reliability and performance of the phospho-tau assay was monitored using 5 pooled CSF samples, covering the performance range of the assay.

Statistical Methods

Normal distribution of CSF-tau, A$\beta$42 and phospho-tau were tested using the Shapiro-Wilk test and if normality was rejected, non-parametric (Kruskal-Wallis) tests were used for comparison. For comparisons with the AD or control group, p-values were adjusted using Dunn's multiple comparison test. Receiver operating curve (ROC) analysis was used to examine the discriminatory power of tau and phospho-tau between AD and controls, DLB, FTD or Parkinson-related conditions, respectively (Hanley and McNeil, 1983). Possible correlations were determined with the Spearman rank correlation coefficient.

CSF-phospho-tau Levels in the Different Neurological Disease Groups

Overall 294 CSF samples were collected from 8 centers. Transportation of CSF samples from one center took longer than 5 days and samples were thawed during transportation. Consequently, new aliquots of these CSF samples were reshipped, apart from one CSF sample (FTD). Five samples from center 2 (5 FTD) and 5 from center 8 (5 PD) were also not assayed because the amount of CSF that was shipped was not sufficient to perform all tests. In summary, 283 CSF samples from the different diagnostic groups (40 controls, 80 AD, 43 DLB, 69 FTD, 15 PD, 15 PSP, 16 MSA and 5 CBD) were assayed for at least one of the biochemical markers (see Table 1). CSF samples were collected between 1985 and 1999. The percentage of males in the group of patients with DLB is high, as expected.

The levels of phospho-tau and their confidence intervals were determined on five QC samples which were used to monitor the performance of the phospho-tau tests. Values for all QC samples fell within the established criteria (results not shown).

Center effects were observed for A$\beta$42 and tau, but not for phospho-tau in the AD group. An effect of freeze-thawing was observed (p<0.0001) for A$\beta$42, but not for tau and phospho-tau and was particularly pronounced in the AD and DLB groups. The effect was further confirmed in the analysis of CSF from center 03. These samples have been assayed previously on site for both tau and A$\beta$42 and were re-assayed at Innogenetics (Gent, Belgium) after two freeze-thaw cycles. An overall 20% reduction of CSF-A$\beta$42 was observed in 8 of the 10 control samples.

No effect of age on the different markers was observed in any of the diagnostic groups. No significant correlation was found between a biomarker and MMSE in the male or female AD group or the total AD group, except for tau and MMSE in the total group (Spearman, r=−0.275[−0.491, −0.059], p=0.01). ApoE genotype did not correlate with CSF-tau or CSF-phospho-tau levels, while a significant correlation was observed for CSF-Aβ42 (Spearman, r=−0.263 [−0.434, −0.093], p=0.003).

Normality was rejected for Aβ42, tau and phospho-tau in all groups and thus analyses were performed using nonparametric tests (Table 1). Significantly increased CSF-tau levels were present in the AD (p<0.001) and FTD group (p<0.05) compared to the control group. Although CSF-tau levels were increased in FTD, levels were significantly higher in the AD group (p<0.01). Using PSP as a reference group, in addition to AD and FTD, CBD had significantly higher CSF-tau levels (p<0.05). For phospho-tau a similar pattern was observed when AD and controls were used to compare. Significantly decreased Aβ42 levels are only observed in the AD (p<0.001) and DLB group (p<0.05) compared to the control group and comparing Aβ42 levels of all groups with the AD group shows a clearly significant difference between AD and FTD (p<0.001). Since in all the Parkinson-related conditions, except CBD, mean levels of biomarkers were within the normal range, these groups were treated as one group in the subsequent analysis.

The strong correlation between tau and phospho-tau for all patients, independent of the diagnostic group (y=0.75x+ 4.6, r=0.904, p<0.001) suggests that the discrimination between AD and other groups obtained with tau can also be obtained with phospho-tau. Using ROC analysis, the discriminative power of total tau with that of phospho-tau was compared. A significant difference between tau and phospho-tau was observed for discriminating AD versus FTD and AD versus DLB, while no difference was observed for AD compared to controls or to the Parkinson-related conditions (Table 2). Since males are overrepresented in the DLB group, the ROC analysis was also performed for male AD versus male DLB with an AUC of 0.800±0.057, comparable to females and males together.

Using the previously established discrimination line that combines CSF-tau and CSF-β-amyloid$_{42}$ (Aβ$_{42}$=240+1.18 tau) (Hulstaert et al., 1999), the sensitivity (98% (CI 91–99%)) and specificity for the control population (73% (CI 56–85%)) was comparable to the previous studies. The specificity of this discrimination line for FTD is 77% (CI 66–85%)), for DLB 67% (CI 52–80%)) and for the Parkinson-related conditions 68% (CI 50–81%)).

REFERENCES

Andreadis A., Brown W., Kosik K. (1992) Structure and novel exons of the human tau gene. Biochem. 31: 10626–10633.

Andreasen N., Vanmechelen E., Van de Voorde A., Davidsson P., Hesse C., Tarvonen S., Räihä I., Sourander L., Winblad B., Blennow K. (1998) Cerebrospinal fluid tau protein as a biochemical marker for Alzheimer's disease: a community-based follow-up study. J. Neurol. Neurosurg. Psychiatry 64: 298–305.

Andreasen N., Minthon L., Clarberg A., Davidsson P., Gottfries J., Vanmechelen E., Vanderstichele H., Winblad B., Blennow K. (1999a) Sensitivity, specificity and stability of CSF-tau in AD in a community-based patient sample. Neurology 53: 1488–1494.

Andreasen N., Hesse C., Davidsson P., Minthon L., Wallin A., Winblad B., Vanderstichele H., Vanmechelen E., Blennow, K. (1999b) Cerebrospinal fluid beta-amyloid (1–42) in Alzheimer disease: differences between early- and late-onset Alzheimer disease and stability during the course of disease. Arch. Neurol. 56: 673–680.

Anonymous (1994) Clinical and neuropathological criteria for frontotemporal dementia. The Lund and Manchester Groups. J. Neurol. Neurosurg. Psychiatry 57: 416–418.

Arbit E., Cheung N. K., Yeh S. D., Daghighian F., Shang J. J., Cordon-Cardo C., Pentlow K., Canete A., Finn R., Larson S. M. (1995) Quantitative studies of monoclonal antibody targeting to disialogangliosid GD2 in human brain tumors. Eur. J. Nucl. Med. 22: 419–426.

Ballard C., Grace J., McKeith I., Holmes C. (1998) Neuroleptic sensitivity in dementia with Lewy bodies and Alzheimer's disease. Lancet 351: 1032–3.

Blermow K., Wallin A., Agren H., Spenger C., Siegfried J., Vanmechelen E. (1995) Tau protein in cerebrospinal fluid: a biochemical marker for axonal degeneration in Alzheimer disease? Mol. Chem. Neuropathol. 26: 231–245.

Bramblett G., Goedert M., Jakes R., Merrick S., Trojanowski J., Lee V. (1993) The abnormal phosphorylation of tau at Ser396 in Alzheimer's disease recapitulates phosphorylation during development and contributes to reduced microtubule binding. Neuron. 10: 1089–1099.

Brion J., Passareiro J., Nunez J., Flament-Durand J. (1985) Mise en evidence immunologique de la proteine tau au niveau des lesions de degenerescence neurofibrillaire de la maladie d'Alzheimer. Arch. Biol. 95: 229–235.

Brun A. (1993) Frontal lobe degeneration of non-Alzheimer type revisited. Dementia 4: 126–131.

Buee L., Delacourte A. (1999) Comparative biochemistry of tau in progressive supranuclear palsy, corticobasal degeneration, FTDP-17 and Pick's disease. Brain Pathol. 9: 681–693.

Colosimo C., Albanese A., Hughes A. J., de Bruin V. M., Lees, A. J. (1995) Some specific clinical features differentiate multiple system atrophy (striatonigral variety) from Parkinson's disease. Arch. Neurol. 52: 294–298.

Delacourte A., Défossez A. (1986) Alzheimer's disease: Tau proteins, the promoting factors of microtubule assembly, are major components of paired helical filaments. J. Neurol. Sci. 76: 173–180.

Delacourte A., Flament S., Dibe E., Hublau P., Sablonniere B., Hemon B., Sherrer V., Defossez A. (1990) Pathological proteins Tau64 and 69 are specifically expressed in the somatodendritic domain of the degenerating cortical neurons during Alzheimer's disease. Acta Neuropathol. 80: 111–117.

Delacourte A., Buée L., Vermersch P. (1996) Immunochemistry in frontotemporal dementia. In: Pasquier F, Lebert F., Scheltens P. (eds.) Frontotemporal dementia. ICG Publications, Dordrecht, The Netherlands. pp. 115–124.

Ebly E. M., Parhad I. M., Hogan D. B., Fung T. S. (1994) Prevalence and types of dementia in the very old: results from the Canadian Study of Health and Aging. Neurology 44: 1593–1600.

Flament S., Delacourte A. (1990) Tau Marker? Nature 346: 6279.

Galasko D., Chang L., Motter R., Clark C. M., Kaye J., Knopman D., Thomas R., Kholodenko D., Schenk D., Lieberburg I., Miller B., Green R., Basherad R., Kertiles L., Boss M. A., Seubert P. (1998) High cerebrospinal fluid tau and low amyloid beta42 levels in the clinical diagnosis of Alzheimer disease and relation to apolipoprotein E genotype. Arch. Neurol. 55: 937–945.

Goedert M., Spillantini M. G., Jakes R., Rutherford D., Crowther R. A. (1989) Multiple isoforms of human microtubule-associated protein tau: sequences and localization in neurofibrillary tangles of Alzheimer's disease. Neuron 3: 519–526.

Goedert M., Spillantini M. G., Cairns N. J., Crowther R. A. (1992) Tau proteins of Alzheimer paired helical filaments:

abnormal phosphorylation of all six brain isoforms. Neuron 8: 159–168.

Goedert M., Jakes R., Crowther R., Six J., Lübke U., Vandermeeren M., Cras P., Trojanowski J. Q., Lee V. (1993) The abnormal phosphorylation of tau protein at serine 202 in Alzheimer's disease recapitulates phosphorylation during development. Proc. Natl. Acad. Sci. (USA) 90: 5066–5070.

Goedert M., Jakes R., Crowther R. A., Cohen P., Vanmechelen E., Vandermeeren M., Cras P. (1994) Epitope mapping of monoclonal antibodies to the paired helical filaments of Alzheimer's disease: identification of phosphorylation sites in tau protein. Biochem. J. 301: 871–877.

Goedert M., Crowther R. A., Spillantini M. G. (1998) Tau mutations cause frontotemporal dementias. Neuron 21: 955–958.

Golbe L. I., Davis P. H. (1993) Progressive supranuclear palsy. Baltimore: Williams & Wilkins.

Greenberg S., Davies P. (1990) A preparation of Alzheimer paired helical filaments that displays distinct tau proteins by polyacrylamide gel electrophoresis. Proc. Natl. Acad. Sci. USA 87: 5827–5831.

Grundke-Iqbal I., Iqbal K., Tung Y., Quinlan M., Wisniewski H., Binder L. (1986) Abnormal phosphorylation of the microtubule-associated protein (tau) in Alzheimer's cytoskeletal pathology. Proc. Natl. Acad. Sci. (USA) 83: 4913–4917.

Gustafson L. (1993) Clinical picture of frontal lobe degeneration of non-Alzheimer type. Dementia 4: 143–148.

Hanger D. P., Betts J. C., Loviny T. L., Blackstock W. P., Anderton B. H. (1998) New phosphorylation sites identified in hyperphosphorylated tau (paired helical filament-tau) from Alzheimer's disease brain using nanoelectrospray mass spectrometry. J. Neurochem. 71: 2465–2476.

Hanley J. A., McNeil B. J. (1983) A method of comparing the areas under receiver operating characteristic curves derived from the same cases. Radiology 148: 839–843.

Hasegawa M., Morishima-Kawashima M., Takio K., Suzuki M., Titani K., Ihara Y. (1992) Protein sequence and mass spectrometric analyses of tau in Alzheimer's disease brain. J. Biol. Chem 267: 17047–17054.

Himmler A. (1989) Structure of the bovine tau gene: alternatively spliced transcripts. Mol. Cell Biol. 9(4): 1389–96.

Hooten W. M., Lyketsos C. G. (1998) Differentiating Alzheimer's disease and frontotemporal dementia: receiver operator characteristic curve analysis of four rating scales. Dement. Geriatr. Cogn. Disord. 9: 164–174.

Huang Q., He G., Lan Q., Li X., Qian Z. Chen J. Lu Z., Du Z. (1996) Target imaging diagnosis of human brain glioma. Clinical analysis of 40 cases. Nucl. Med. Commun. 17: 311–316.

Hulstaert F., Blennow K., Ivanoiu A., Schoonderwaldt H. C., Riemenschneider M., De Deyn P. P., Bancher C., Cras P., Wiltfang J., Mehta P. D., Iqbal K., Pottel H., Vanmechelen E., Vanderstichele H. (1999). Improved discrimination of AD patients using beta-amyloid(1–42) and tau levels in CSF. Neurology 52: 1555–1562.

Iqbal K., Grundke-Iqbal I., Smith A., George L., Tung Y., Zaidi T. (1989) Identification and localisation of a Tau peptide to paired helical filaments of Alzheimer's disease. Proc. Natl. Acad. Sci. (USA) 86: 5646–5650.

Ishiguro K., Ohno H., Arai H., Yamaguchi H., Urakami K., Park J. M., Sato K., Kohno H., Imahori K. (1999) Phosphorylated tau in human cerebrospinal fluid is a diagnostic marker for Alzheimer's disease. Neurosci. Lett. 270: 91–94.

Kanai M., Matsubara E., Isoe K., Urakami K., Nakashima K., Arai H., Sasaki H., Abe K., Iwatsubo T., Kosaka T., Watanabe M., Tomidokoro Y., Shizuka M., Mizushima K., Nakamura T., Igeta Y., Ikeda Y., Amari M., Kawarabayashi T., Ishiguro K., Harigaya Y., Wakabayashi K., Okamoto K., Hirai S., Shoji M. (1998) Longitudinal study of cerebrospinal fluid levels of tau, A betal-40, and A betal-42(43) in Alzheimer's disease: a study in Japan. Ann. Neurol. 44: 17–26.

Kondo J., Honda T., Mori H., Hamada Y., Miura R., Ogawara M., Ihara Y. (1988) The carboxyl third of tau is tightly bound to paired helical filaments. Neuron 1: 827–834.

Kosik K. S., Joachim C. L., Selkoe D. J. (1986) Microtubule-associated protein tau is a major antigenic component of paired helical filaments in Alzheimer's disease. Proc. Natl. Acad. Sci. (USA) 83: 4044–4048.

Ksiezak-Reding H., Liu W. K., Yen S. H. (1992) Brain Res. 597: 209–219.

Langston J. W., Widner H., Goetz C. G., Brooks D., Fahn S., Freeman T., Watts R. (1992). Core assessment program for intracerebral transplantations (CAPIT). Mov. Disord .7: 2–13.

Lebert F., Pasquier F., Souliez L., Petit H. (1998) Tacrine efficacy in Lewy body dementia. Int.J.Geriatr.Psychiatry 13: 516–519.

Lee V., Balin B., Otvos L., Trojanowski J. (1991) A68: a major subunit of paired helical filaments and derivatized forms of normal tau. Science 251(4994): 675–8.

Levy R., Eagger S., Griffiths M., Perry E., Honavar M., Daen A., Lantos P. (1994) Lewy bodies and response to tacrine in Alzheimer's disease. Lancet 343: 176–178.

Lewis S., Wang D., Cowan N. (1988) Microtubule-associated protein MAP2 shares a microtubule binding motif with Tau protein. Science 242: 936–939.

Mariani G., Lasku A., Pau A., Villa G., Motta C., Calcagno G., Taddei G. Z., Castellani P., Syrigos K., Dorcaratto A., Epenetos A. A., Zardi L., Viale G. A. (1997) A pilot pharmacokinetic and immunoscintigraphic study with the technetium-99m labelled monoclonal antibody BC-1 directed against oncofetal fibronectin in patients with brain tumours. Cancer 15: 2484–2489.

McKeith I. G., Galasko D., Kosaka K., Perry E. K., Dickson D. W., Hansen L. A., Salmon D. P., Lowe J., Mirra S. S., Byrne E. J., Lennox G., Quinn N. P., Edwardson J. A., Ince P. G., Bergeron C., Burns A., Miller B. L., Lovestone S., Collerton D., Jansen E. N., Ballard C., de Vos R. A., Wilcock G. K., Jellinger K. A., Perry, R. H. (1996) Consensus guidelines for the clinical and pathologic diagnosis of dementia with Lewy bodies (DLB): report of the consortium on DLB international workshop. Neurology 47: 1113–1124.

McKeith I. G., O'Brien J. T., Ballard C. (1999) Diagnosing dementia with Lewy bodies. Lancet 354: 1227–1228.

Mc Khann G., Drachman D., Folstein M., Katzman R., Price D., Stadlan E. M. (1984) Clinical diagnosis of Alzheimer's disease: report on the NINCDS-ADRDA Work group under the auspices of department of health and human services task force on Alzheimer's disease. Neurology 34: 939–944.

Perry E. K., Haroutunian V., Davis K. L., Levy R., Lantos P., Eagger S., Honavar M., Dean A., Griffiths M., McKeith I. G., et al. (1994) Neocortical cholinergic activities differentiate Lewy body dementia from classical Alzheimer's disease. Neuroreport 5: 747–749.

Rinne J. O., Lee M. S., Thompson P. D., Marsden C. D. (1994). Corticobasal degeneration. A clinical study of 36 cases. Brain 117 (Pt 5): 1183–1196.

Sandrock D., Verheggen R., Helwig A. T., Munz D. L., Markakis E., Emrich D. (1996) Immunoscintigraphy for the detection of brain abscesses. Nucl. Med. Commun. 17: 311–316.

Selden S., Pollard T. (1983) Phosphorylation of microtubule-associated proteins regulates their interaction with actin filaments. J. Biol. Chem. 258(11): 7064–71.

Spillantini M. G., Goedert M. (1998) Tau protein pathology in neurodegenerative diseases. Trends Neurosci. 21: 428–433.

Tamada K., Fujinaga S., Watanabe R., Yamashita R., Takeuchi Y., Osano M. (1995) Specific deposition of passively transferred monoclonal antibodies against herpes simplex virus type 1 in rat brain infected with the virus. Microbiol-Immunol. 39: 861–871.

Tomlinson B. E., Corsellis J. A. N. (1984) Ageing and the demntias. In: Hume Adams J., Corsellis J. A. N., Duchen L. W. (eds.) Greenfield's neuropathology. Edward Arnold, London, UK. pp. 951–1025.

Vandermeeren M., Mercken M., Vanmechelen E., Six J., Van de Voorde A., Martin J. J., Cras P. (1993) Detection of tau proteins in normal and Alzheimer's disease cerebrospinal fluid with a sensitive sandwich enzyme-linked immunosorbent assay. J. Neurochem. 61: 1828–1834.

Van de Voorde A., Vanmechelen E., Vandermeeren M., Dessaint F., Beeckman W., Cras P. (1995) Detection of tau in cerebrospinal fluid. In: Iqbal K., Mortimer J. A., Winblad B. and Wisniewski H. M. Alzheimer's disease: Research Advances in Alzheimer's Disease and Related Disorders. John Wiley & Sons, Ltd. Chicester, New York, Brisbane, Toronto, Singapore. pp. 189–195.

Vanderstichele H., Blennow K., D'Heuvaert N., Buyse M. -A., Wallin A., Andreasen N., Seubert P., Van de Voorde A., Vanmechelen, E. (1998) Development of a specific diagnostic test for measurement of β-amyloid(1–42) [(βA₄(1–42)] in CSF. In: Fisher A., Hanin A. and Yoshida M. Progress in Alzheimer's and Parkinson's diseases. Plenum Press, New York and London. pp. 773–778.

Vermersch P., Bordet R., Ledoze F., Ruchoux M. M., Chapon F., Thomas P., Destee A., Lechevallier B., Delacourte A. (1995) C R Demonstration of a specific profile of pathological Tau proteins in frontotemporal dementia cases. Acad. Sci. 318: 439–445.

Vigo-Pelfrey C., Seubert P., Barbour R., Blomquist C., Lee M., Lee D., Coria F., Chang L., Miller B., Lieverburg I., et al. (1995) Elevation of microtubule-associated protein tau in the cerebrospinal fluid of patients with Alzheimer's disease. Neurology 45: 788–793.

Wakabayashi T., Yoshida J., Okada H., Sugita K., Itoh K., Tadokoro M., Ohshima M. (1995) Radioimaging of human glioma by indium-11 labelled G-22 anti-glioma monoclonal antibody. Noshuyo-Byori 12: 105–110.

Wilcock G. K., Scott M. I. (1994) Tacrine for senile dementia of Alzheimer's or Lewy body type. Lancet 344: 544–544.

Wilson J D, Braunwald E, Isselbacher K J, Petersdorf R G, Martin J B, Fauci A S, Root R K (1991) Harrison's Principles of Internal Medicine, 12th Edition, McGraw-Hill Inc, NY, USA.

Wood J., Mirra S., Pollock N., Binder L. (1986) Neurofibrillary tangles of Alzheimer's disease share antigenic determinants with the axonal mirotubule-associated protein tau. Proc. Natl. Acad. Sci. (USA) 83: 4040–4043.

What is claimed is:

1. A method for aiding in the determination of whether an individual is suffering from Alzheimer's disease (AD) versus dementia with Lewy bodies DLB, frontotemporal dementia (FTD), Parkinson's disease (PD), multi-system atrophy (MSA), or progressive supranuclear palsy (PSP), the method comprising:

(a) determining the level of phospho-tau in a cerebrospinal fluid (CSF) sample obtained from said individual;

(b) comparing the determined level of phospho-tau in the CSF sample obtained from said individual with a range of phospho-tau levels previously defined as characteristic for CSF samples obtained from AD, DLB, FTD, PD, MSA, or PSP patients;

(c) concluding from the comparison in step (b) whether said individual is suffering from Alzheimer's disease or from dementia with Lewy bodies, frontotemporal dementia, Parkinson's disease, multi-system atrophy, progressive or supranuclear palsy; whereby a phospho-tau level in the range previously defined as characteristic for CSF samples obtained from AD patients is an indication that the individual is suffering from AD; whereby a phospho-tau level in a range previously defined as characteristic for CSF samples obtained from DLB patients is an indication that the individual is suffering from DLB; whereby a phospho-tau level in a range previously defined as characteristic for CSF samples obtained from FTD patients is an indication that the individual is suffering from FTD; whereby a phospho-tau level in a range previously defined as characteristic for CSF samples obtained from PD patients is an indication that the individual is suffering from PD; whereby a phospho-tau level in a range previously defined as characteristic for CSF samples obtained from MSA patients is an indication that the individual is suffering from MSA; and whereby a phospho-tau level in a range previously defined as characteristic for CSF samples obtained from PSP patients is an indication that the individual is suffering from PSP.

2. A method for aiding in the determinations of whether an individual is suffering from Alzheimer's disease (AD) versus dementia with Lewy bodies (DLB) versus frontotemporal dementia (FTD) the method comprising:
  (a) determining the level of phospho-tau in a cerebrospinal fluid (CSF) sample from said individual;
  (b) comparing the determined level of phospho-tau in the CSF sample obtained from said individual with a range of phospho-tau levels previously defined as characteristic for CSF samples obtained from AD, DLB, or FTD patients, respectively;
  (c) determining from the comparison in step (b) whether said individual is suffering from Alzheimer's disease or from dementia with Lewy bodies or from frontotemporal dementia, whereby a phospho-tau level in a range previously define as characteristic for CSF samples obtained from AD patients is an indication that said individual is suffering from AD; whereby a phospho-tau level in a range previously define as characteristic for CSF samples obtained from DLB patients is an indication that the individual is suffering from DLB; and whereby a phospho-tau level in a range previously define as characteristic for CSF samples obtained from FTD patients is an indication that the individual is suffering from FTD.

3. The method of claim 2 wherein the range of phospho-tau levels previously defined as characteristic for CSF samples obtained from AD patients is determined by measuring phospho-tau levels in a plurality of persons known to have AD, wherein the range of phospho-tau levels previously defined as characteristic for CSF samples obtained from DLB patients is determined by measuring phospho-tau levels in a plurality of persons known to have DLB, and wherein the range of phospho-tau levels previously defined as characteristic for CSF samples obtained from FTD patients is determined by measuring phospho-tau levels in a plurality of persons known to have FTD.

4. The method of claim 2 wherein the range of phospho-tau levels previously defined as characteristic for CSF samples obtained from AD patients has a median value of about 14.7 picomolar and $25^{th}$ and $75^{th}$ percentile values of about 11.6 picomolar and about 19.1 picomolar respectively; wherein the range of phospho-tau levels previously defined as characteristic for CSF samples obtained from DLB patients has a median value of about 8.1 picomolar and $25^{th}$ and $75^{th}$ percentile values of about 6.1 picomolar and about 10.0 picomolar respectively; and wherein the range of phospho-tau levels previously defined as characteristic for CSF samples obtained from FTD patients has a median value of about 9.4 picomolar and $25^{th}$ and $75^{th}$ percentile values of about 8.2 picomolar and about 12.3 picomolar respectively.

5. A method for aiding in the determination of whether an individual is suffering from Alzheimer's disease (AD) versus a non-AD neurological disease selected from the group consisting of: dementia with Lewy bodies DLB, frontotemporal dementia (FTD), Parkinson's disease (PD), multi-system atrophy (MSA), and progressive supranuclear palsy (PSP), the method comprising:
  (a) determining the level of phospho-tau in a cerebrospinal fluid (CSF) sample obtained from said individual;
  (b) comparing the determined level of phospho-tau in the CSF sample obtained from said individual with a range of phospho-tau levels previously defined as characteristic for CSF samples obtained from AD, DLB, FTD, PD, MSA, or PSP, patients;
  (c) concluding from the comparison in step (b) whether said individual is suffering from Alzheimer's disease or a non-AD neurological disease selected from the group consisting of: dementia with Lewy bodies, frontotemporal dementia, Parkinson's disease, multi-system atrophy, or progressive supranuclear palsy; whereby a phospho-tau level in the range previously defined as characteristic for CSF samples obtained from AD patients is an indication that the individual is suffering from AD; and,
    whereby a phospho-tau level which is not in the range previously defined as characteristic for CSF samples obtained from AD patients is an indication that the individual is suffering from a non-AD neurological disease selected from the group consisting of: DLB, FTD, PD, MSA, and PSP.

* * * * *

SEQUENCE LISTING

```
<160> NUMBER OF SEQ ID NOS: 1

<210> SEQ ID NO 1
<211> LENGTH: 34
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (28)..(28)
<223> OTHER INFORMATION: PHOSPHORYLATION THREONINE

<400> SEQUENCE: 1

Pro Arg Gly Ala Ala Pro Pro Gly Gln Lys Gly Gln Ala Asn Ala Thr
    1               5                   10                  15
    Arg Ile Pro Ala Lys Thr Pro Pro Ala Pro Lys Thr Pro Pro Ser Ser
                20                  25                  30
    Gly Glu
```